United States Patent [19]

Baker

[11] 4,115,408

[45] Sep. 19, 1978

[54] CONVERSION OF POLY(TETRAMETHYLENE ETHER) GLYCOL IN AQUEOUS EFFLUENT STREAM TO TETRAHYDROFURAN

[75] Inventor: Melvin Charles Baker, Youngstown, N.Y.

[73] Assignee: E.I. DuPont de Nemours and Company, Wilmington, Del.

[21] Appl. No.: 822,271

[22] Filed: Aug. 5, 1977

[51] Int. Cl.² .......................................... C07D 307/08
[52] U.S. Cl. ............................. 260/346.11; 260/615 B
[58] Field of Search ......................... 260/346.11, 615 B

[56] References Cited

U.S. PATENT DOCUMENTS 3,925,484   12/1975   Baker ................................ 260/615 B

*Primary Examiner*—Henry R. Jiles
*Assistant Examiner*—Bernard Dentz

[57] ABSTRACT

A process for removing poly(tetramethylene ether) glycol from dilute aqueous acidic effluent streams thereof comprising the steps of (1) maintaining the stream in the liquid phase at a temperature above about 150° C for a period of at least about 15 minutes and (2) removing tetrahydrofuran therefrom.

5 Claims, 1 Drawing Figure

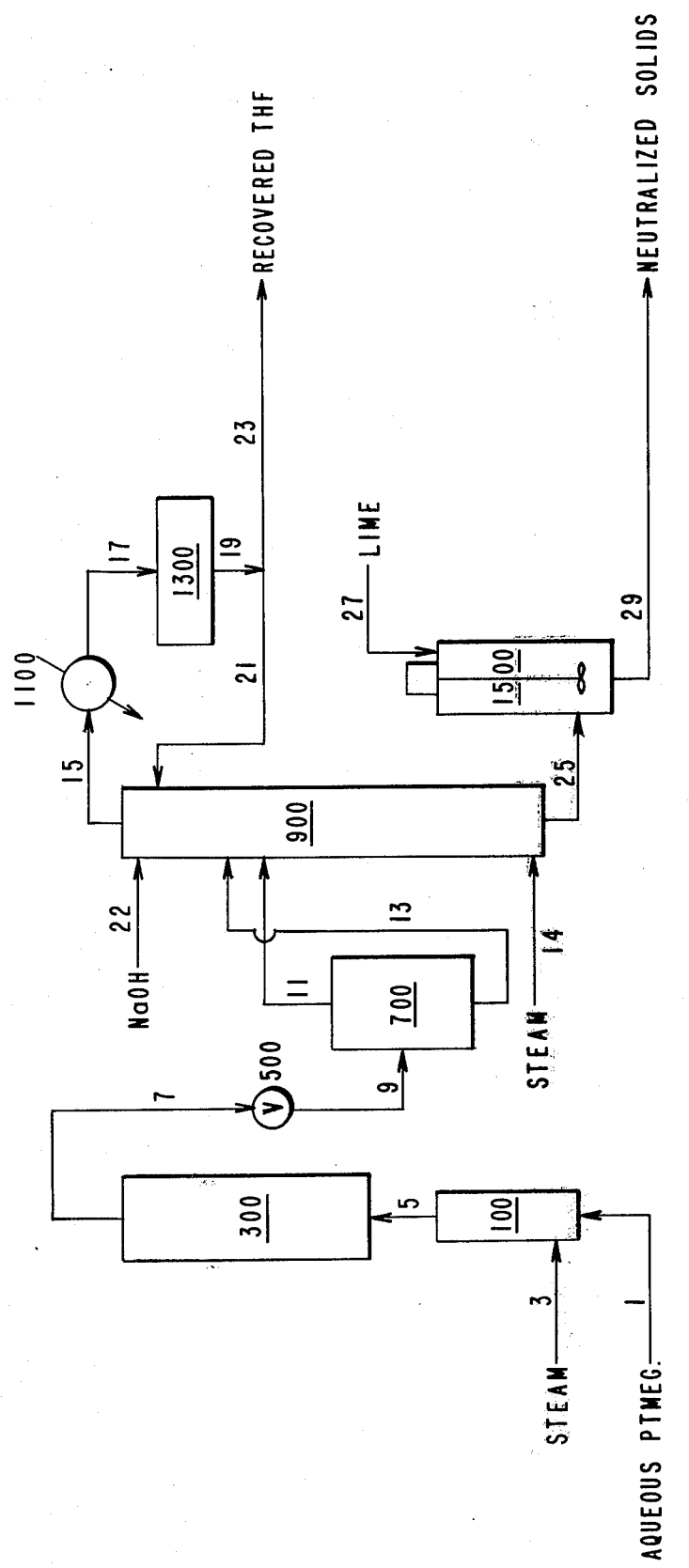

CONVERSION OF POLY(TETRAMETHYLENE ETHER) GLYCOL IN AQUEOUS EFFLUENT STREAM TO TETRAHYDROFURAN

FIELD OF THE INVENTION

The invention is directed to a process for removing esters of poly(tetramethylene ether) glycols from dilute aqueous effluent streams. More particularly, the invention is directed to the removal of such materials by depolymerization and recovery of the resultant products.

BACKGROUND OF THE INVENTION

Poly(tetramethylene ether) glycol is widely used as the polyol component with isocyanates to make thermoplastic polyurethanes. In this application, the poly(tetramethylene ether) glycol imparts both flexibility and hydrolytic stability to polyurethane products.

Poly(tetramethylene ether) glycol, which for convenience will be referred to hereinafter as PTMEG, is made by polymerizing anhydrous tetrahydrofuran (THF) in the presence of an acid catalyst such as fluosulfonic acid. When using an acid catalyst, the polymer is converted in part to esters which are hydrolyzed with water to obtain higher, more economic yields of the polyol product. In U.S. Pat. No. 2,751,419 to Hill and Schulze, it is disclosed that this may be accomplished by "drowning" the polymerization system with hot water. Unreacted tetrahydrofuran is then removed from the resultant aqueous dispersion by conventional stream stripping.

The acidic aqueous dispersion of impure PTMEG is then subjected to washing with water. The washed PTMEG product dispersion is neutralized with lime, decanted to remove most of the water and solids, which are recirculated to the washing operation. The product PTMEG is recovered by drying and filtering.

A substantial amount of aqueous acidic effluent results from the PTMEG washing. Because this stream is acidic and also because it contains small amounts of organics, disposal of this stream becomes a problem; and furthermore, the yield of PTMEG is substantially reduced by losses of product in the effluent from the washing step. For example, the yield loss from this source alone will be on the order of about 2% for relatively high molecular weight grades, but rises to above 10% for the lower molecular weight grades. Thus, from the standpoint of effluent treatment, it would be desirable to lower the chemical oxidation demand (COD) to the effluent stream. Furthermore, from the standpoint of process economics, it would be desirable to reduce the amount of materials wasted whether as raw material or as PTMEG product.

BRIEF SUMMARY OF THE INVENTION

It has now been discovered that poly(tetramethylene ether) glycol contained in low concentration in aqueous acidic effluent streams can be economically depolymerized and cyclized to form tetrahydrofuran, which is recovered from the effluent stream and recycled to a polymerization process to form additional PTMEG. In particular, the invention is directed to a process for removing PTMEG from aqueous acidic streams in which it is dissolved comprising the sequential steps of (1) maintaining the stream in the liquid phase at a temperature above about 150° C for a period of at least about 15 minutes, by which PTMEG is depolymerized and THF is reformed therefrom and (2) removing THF from the stream.

DISCUSSION OF THE PRIOR ART

It is known that PTMEG will depolymerize on heating in the presence of anhydrous inorganic acids such as $H_2SO_4$, and that the rate of depolymerization is a function of the weight ratio of acid as well as the temperature. Depolymerization carried out in this manner is non-selective, i.e., it depolymerizes both high and low molecular materials. From U.S. Pat. No. 3,925,484 to Baker, it is also known that PTMEG can be depolymerized at 120°-150° C in an essentially anhydrous system by contact with crosslinked acid-form ion exchange resins. The depolymerization carried out in this manner is, however, selective to the low molecular weight components of the polymer. Furthermore, atmospheric distillation studies showed that the rate of depolymerization of PTMEG in dilute aqueous streams in the presence of dilute acids up to about 50% was too slow to be a practicable means of removing PTMEG. For example, using 20% $H_2SO_4$ resulted in the recovery of only about 10% of the THF values contained in the stream; and using 50% $H_2SO_4$ resulted in the recovery of only about 40% of the THF values. It is therefore apparent that such prior art processes would not reduce COD to acceptable levels. Furthermore, it was found that in the distillation operation, the acidic system ($H_2SO_4$ and HF derived from the fluosulfonic acid) was highly corrosive even to Monel[1] alloy.

[1] Trademark of the International Nickel Co., Inc., Huntington Alloy Products Div., Huntington, WV, for alloy corrosion-resistant alloy containing about 66% Ni and 31% copper.

DETAILED DESCRIPTION OF THE INVENTION

To obtain practicable levels of depolymerization of PTMEG and the concomitant formation of THF, it is essential that the process be carried out at temperatures of 150°-200° C. At temperatures below about 150° C, the extent of depolymerization is too low; at temperatures above about 200° C, the pressure required to keep the system liquid is so high as to require excessive capital expenditures for equipment capable of withstanding those pressures. A temperature range of 160°-190° C is preferred and a range of 170°-180° C appears to be optimum for most operations. Heating the effluent stream to the proper reaction temperature can be accomplished either indirectly or directly. However, direct steam addition is both economical and effective.

To obtain adequate THF recovery and to avoid excessively corrosive conditions, it is necessary to maintain the reaction system in the liquid phase. Thus, the process must be carried out at a pressure sufficient to prevent any substantial vaporization of the system. In particular, the pressure of the system must exceed the vapor pressure of water at the operating temperature. For example, at 150° C the pressure of the reaction system must exceed 54 psig; and at 200° C, the pressure must exceed 211 psig. It will be noted that when pressures below the vapor pressure of THF are used, part of the THF resulting from the reaction will be vaporized. However, this does not contribute to the corrosivity of the system. Because it is easier to control, the reaction system when it is essentially completely in the liquid phase, it is preferred that the THF likewise be kept in solution. Nevertheless, it is essential that the unreacted effluent stream itself — water and PTMEG — remain in the liquid phase.

The concentration of acid in the effluent stream to be heated is not narrowly critical in the sense of operability of the invention because the acid functions as a catalyst in the process of the invention. However, the amount of acid in the effluent stream does affect the amount of THF values that are present in the effluent stream prior to the depolymerization reaction. More particularly, it is found that the amount of PTMEG is related directly to the acid concentration. That is, if more acid is present, more polymer is dissolved. Therefore, at least about 2% wt. acid is preferred in the process and up to about 15% wt. is quite normal. A range of 3-12% wt. acid is still further preferred. Though the acid level in the stream being treated can be adjusted by dilution or acid addition, it will ordinarily not be necessary to do so. The acid concentration of the PTMEG effluent will usually be a function of the degree of washing and the molecular weight of the PTMEG. As used herein, the term "% wt. acid" refers to hydrogen ion concentration determined by titration with standard aqueous caustic and expressed as "% wt. $H_2SO_4$". It should be noted, however, that the invention is equally applicable to acidic aqueous PTMEG streams in which the hydrogen ions are derived from other acids. Likewise, the acidity of the stream being treated can be adjusted using other acids, particularly the mineral acids.

The time of reaction is important to the economics of the reaction in that at least about 15 minutes exposure to the reaction temperature is needed to obtain adequate levels of depolymerization. However, no significant additional reaction is observed after more than about 2 hours. Reaction times of at least 0.5 hour and especially 1 hour are preferred. The reactor for the process can be of virtually any configuration since its sole function is to hold the liquid at the desired operating temperature and pressure for the required time. The reactor can be operated in either a batchwise or continuous manner. Furthermore, so long as the water portion of the stream does not become vaporized, the vessel can be fabricated from materials such as copper or copper alloys.

Tetrahydrofuran (THF) produced by the depolymerization reaction is dissolved in the water of the stream as it leaves the reactor, but is readily removed by simple fractional distillation, which is most economically carried out at nearly atmospheric pressure. Thus, the depolymerized effluent stream is preferably passed through a pressure let-down valve upstream of the fractionating column. The THF is recovered in the column overhead fraction with a small amount of water therein (5-10% wt.), depending upon column operating conditions such as reflux ratio and temperature in the top of the column. The bottoms fraction containing mostly water, acids, and only small amounts (less than 0.5% wt.) of PTMEG remain dissolved therein.

A recovery level of THF-PTMEG of 70% is attainable quite readily with the process of the invention and commercial scale recovery levels of over 80% have been obtained on a routine basis. COD levels are reduced proportionately.

Within the above-preferred limits of time, temperature and acid level, the concentration of PTMEG in the effluent stream is not critical. Though from the viewpoint of operability of the process much higher amounts could be effectively treated, THF values in the stream will usually range between about 0.1 and 10% by weight. At equivalent operating conditions of the PTMEG product wash train, the amount of recoverable THF tends to be lower for the higher molecular weight PTMEG product. This can be observed in the following tabulation in which acid and THF levels are given for typical effluents produced in accordance with U.S. Pat. No. 2,751,419 in the manufacture of PTMEG products of various molecular weights.

| Number Average Molecular Weight[2] | 650 | 1000 | 1800 | 2000 |
|---|---|---|---|---|
| THF Values (PTMEG) (% wt.) | 6.0 | 3.0 | 1.0 | 0.7 |
| Hydrogen Ion Concentration (% wt. as $H_2SO_4$) | 12 | 8 | 5 | 4 |

The invention will better be understood by reference to the drawing which consists of a single FIGURE in which a flow diagram of a preferred form of commercial operation of the process is presented schematically.

DETAILED DESCRIPTION OF THE DRAWING

The feed to the process of the invention is a dilute aqueous effluent from a commercial PTMEG manufacturing facility resulting from purification of PTMEG by the process taught by U.S. Pat. No. 2,751,419. The effluent feedstream had the following composition by weight:

| Water | 86.5% |
|---|---|
| PTMEG, dissolved | 2.3 |
| PTMEG, dispersed | 0.3 |
| Acid, as $H_2SO_4$ | 10.6 |
| Ca Salts | 0.3 |
| | 100.0% |

The dilute PTMEG-containing stream is continuously fed via line 1 to heater 100 in which the stream is heated to about 175° C by the injection of 450 psig steam which is admitted through line 3. The heated stream is then passed via line 5 to the bottom of reactor 300 at a rate such that the residence time within the vessel is about 2 hours. Pressure within the reactor is maintained at about 195 psig, thus the contents of the vessel are maintained in the liquid state. Effluent from the reactor is then passed via line 7 through let-down valve 500 over which the pressure on the stream is lowered to 0-15 psig. The still hot stream is then passed via line 9 to flashing chamber 700 in which about 20% by weight of the stream is vaporized overhead and passed through line 11 into fractionation column 900. To facilitate separation of the THF, the unvaporized bottoms from the flasher is fed to the fractionation column via line 13 to a point above the level at which the flasher overhead is introduced. Stripping steam is introduced into the bottom of fractionation column 900 through line 14 and a small flow of aqueous NaOH (50% by weight) is introduced via line 22 into the top of the column to reduce corrosion in that zone. Vaporized overhead product from column 900 is removed from the column through line 15 to condenser 1100 in which it is essentially completely condensed by cooling from about 67° C to about 20° C. The condensate is then passed via line 17 to accumulator vessel 1300. The overhead product from the fractionation column has the following composition by weight:

| Water | 6% |
|---|---|
| THF | 94% |

Condensed overhead product is removed from the accumulator via line 19 and is then split into two parts. A major proportion of the overhead product, which is mainly THF, is recycled as reflux to the column via line 21. The remainder of the recovered THF is sent via line 23 to storage. The THF recovered by this process upon drying was found to be a satisfactory raw material for polymerization to form PTMEG.

The bottoms fraction from column 900 is essentially free of THF and has the following composition by weight:

| | |
|---|---|
| Water | 90.4% |
| PTMEG, Dissolved | 0.4 |
| PTMEG, Dispersed | 0.2 |
| Acid, as $H_2SO_4$ | 8.4 |
| Ca Salts | 0.2 |
| $Na_2SO_4$/NaF | 0.4 |
| THF | <0.1 |
| | 100.0% |

Fractionation bottoms product is removed from fractionator 900 through line 25 to stirred reaction vessel 1500. Lime is added via line 27 to the stirred vessel to effect neutralization of the bottoms product. The neutralized bottoms product is then passed through line 29, dewatered and the solids disposed of as waste.

I claim:

1. A process for removing poly(tetramethylene ether) glycol from dilute aqueous acidic streams thereof comprising the sequential steps of
   (a) maintaining the stream in the liquid phase at a temperature above about 150° C for a period of at least about 15 minutes and
   (b) separating tetrahydrofuran therefrom.

2. The process of claim 1 in which the hydrogen ion concentration of the acidic stream is equivalent to 2–15% by weight $H_2SO_4$.

3. The process of claim 1 in which the stream is maintained at 150°–200° C for at least 0.5 hour.

4. The process of claim 1 in which tetrahydrofuran is removed from the stream by vaporization.

5. The process of claim 4 in which the acidic stream from which tetrahydrofuran has been removed is neutralized to effect precipitation of neutralized solids and filtered to separate water from the neutralized solids.

* * * * *